(12) United States Patent
Carli

(10) Patent No.: US 10,870,998 B2
(45) Date of Patent: Dec. 22, 2020

(54) ELECTRONIC TROWEL

(71) Applicant: LATICRETE INTERNATIONAL, INC, Bethany, CT (US)

(72) Inventor: Matthew David Carli, Hamden, CT (US)

(73) Assignee: Laticrete International, Inc., Bethany, CT (US)

( * ) Notice: Subject to any disclaimer, the term of this patent is extended or adjusted under 35 U.S.C. 154(b) by 0 days.

(21) Appl. No.: 16/583,936

(22) Filed: Sep. 26, 2019

(65) Prior Publication Data

US 2020/0109572 A1 Apr. 9, 2020

Related U.S. Application Data

(60) Provisional application No. 62/740,665, filed on Oct. 3, 2018.

(51) Int. Cl.
*E04F 21/24* (2006.01)
*G01N 33/38* (2006.01)
*G01B 21/30* (2006.01)

(52) U.S. Cl.
CPC ............ *E04F 21/241* (2013.01); *G01B 21/30* (2013.01); *G01N 33/383* (2013.01)

(58) Field of Classification Search
CPC ...................... E04F 21/241; E04F 21/161–163
See application file for complete search history.

*Primary Examiner* — Andrew A Horton
(74) *Attorney, Agent, or Firm* — Delio Peterson & Curcio; Kelly M. Nowak

(57) ABSTRACT

Electronic trowels, systems and methods of applying a layer of material using the present electronic trowels. The various electronic trowels include a handle, at least one blade, and one or more sensors residing on or within the trowel. The trowel is for applying a layer of material over a surface area, whereby the one or more sensors detect and collect material installation data during application of the layer of material over the surface area. One or more electronic devices coupled to the one or more sensors receive and analyze the collected installation data for monitoring and controlling the application of the layer of material to ensure a desired end product is achieved. Application errors may be detected before, during, or after the installation process.

18 Claims, 4 Drawing Sheets

| Time | Accelerometer (G-Force) | | | Gyroscope (DPS - Degrees per Second) | | | Magnetometer (µT) | | |
|---|---|---|---|---|---|---|---|---|---|
| <timeMS> | <accelX> | <accelY> | <accelZ> | <gyroX> | <gyroY> | <gyroZ> | <magX> | <magY> | <magZ> |
| 1450 | 0.08 | -0.26 | -0.92 | -4.7 | -28.41 | -61.34 | 153.34 | 26.41 | 41.71 |
| 1460 | -0.06 | -0.05 | -1.06 | -9.51 | -22.56 | -42.13 | 151.54 | 28.21 | 41.11 |
| 1469 | -0.05 | -0.13 | -1.02 | -8.72 | -8.05 | -26.16 | 152.74 | 26.71 | 39.61 |
| 1479 | -0.01 | -0.13 | -0.93 | -17.01 | 7.07 | -28.17 | 153.94 | 26.86 | 39.16 |
| 1488 | 0.19 | -0.12 | -1.29 | -6.52 | 2.07 | -9.09 | 154.09 | 27.46 | 38.56 |
| 1498 | 0.07 | -0.1 | -1.09 | -27.26 | 12.93 | -24.21 | 157.39 | 27.46 | 33.46 |
| 1507 | -0.11 | -0.1 | -1.02 | -9.94 | 21.04 | -7.74 | 155.89 | 28.21 | 28.21 |
| 1517 | 0.05 | -0.24 | -1.04 | -21.16 | 46.77 | -8.78 | 157.24 | 28.36 | 21.46 |
| 1526 | 0.07 | 0.42 | -1.14 | -64.7 | 82.93 | -86.95 | 157.24 | 27.31 | 19.05 |

ELECTRONIC TROWEL

BACKGROUND OF THE INVENTION

1. Field of the Invention

The present invention relates to tools for finishing concrete, plaster, and similar materials, and in particular, trowels having electronics for detecting, monitoring, and controlling trowel usage, trowel performance, material applications, and end-user performance.

2. Description of Related Art

A trowel is a tool often used to mix, apply, spread, shape, and/or smooth loose or aqueous materials. Trowels are often used in gardening, and in the construction industry for applying concrete, cementitious materials (e.g., mortar, grout, etc.), plaster, masonry, drywall, adhesives, and the like. In the construction industry, trowels are used for tiling and laying synthetic flooring. Current trowels include both small hand-held tool trowels or larger power trowels (e.g., larger gasoline or electrically powered walk-behind device with rotating paddles used to finish concrete floors).

Hand-held trowels are typically used in applying cementitious materials, such as, mortars, grouts, adhesives, and the like. In laying flooring or tiling, mortars (e.g., thin set mortars) are applied over a substrate to bond decorative flooring (e.g., tile) to the substrate. In a proper tile installation, the cementitious materials must be applied over a substrate to a predefined thickness and consistency so that the material bonds tile to the substrate for providing an unflawed finished product. If the cementitious material is improperly applied, the resulting finished product may have insufficient bonding and/or support undesirably resulting in a flawed finished product susceptible to debonding and cracking.

Further in cement or tile installation, use of hand-held trowels depends on the skill level of the end-user in providing a consistent, smooth and level surface. While some cementitious materials are available in ready-to-use forms (i.e., do not require mixing prior to use), other materials are provided in a dry or powdered state that require preparation prior to use thereof. In those cementitious materials that require preparation, it is up to the end-user to mix such materials with a proper amount of water to provide the material with a predetermined thickness or density. Although a skilled end-user may be able to produce reasonably accurate work under these conditions, there is no way for a skilled or unskilled end-user to ensure he/she is properly using the trowel, has mixed the cementitious material with the correct ratio of water to material, or is performing an accurate installation that will generate acceptable results.

As trowels are often used to install cementitious materials alone or in combination with tile installations, the use and monitoring of trowel usage and material application is not supported by current trowels.

Accordingly, a need exists in the art for improved systems, methods of making, and the resultant trowels that are capable of sensing and monitoring trowel usage, trowel performance, end-user performance, applied material properties as well as material applications.

BRIEF SUMMARY OF THE INVENTION

The disclosed embodiments of the invention relate to electronic trowels for applying a layer of material. The trowels include a handle, at least one blade, and one or more sensors residing on or within the trowel. The trowel is for applying a layer of material over a surface area, whereby the one or more sensors detect and collect material installation data during application of the layer of material over the surface area. One or more electronic devices coupled to the one or more sensors receive and analyze the collected installation data for monitoring and controlling the application of the layer of material to ensure a desired end product is achieved.

In various embodiments the electronic devices may analyze the collected installation data to identify any errors in the application of the layer of material for correction by an installer either before, during, or after the installation process, or combinations thereof. The one or more sensors may be attached to the handle, to the at least one blade, to a shank of the trowel, or any combination thereof. The one or more sensors may include temperature sensors, location sensors, infrared sensors, ultrasound sensors, pH sensors, movement sensors, and/or optical sensors.

In one or more embodiments, the one or more sensors may detect a height and a pattern of the applied layer of material for determining whether any slumping of ridges of the applied layer of material is present within the applied layer of material. Suitable sensors may include, for instance, infrared sensors or ultrasound sensors, or movement sensors that detect the height and the pattern of the applied layer of material. In other embodiments the one or more sensors may be capable of capturing forces and stresses exerted on the end user for using in ensuring installer safety.

In certain embodiments the one or more sensors may detect working conditions of the application process for determining whether the mixture of the material being applied has a correct proportion of material to water prior to use thereof. These sensors may include, but are not limited to, a density detection sensor, temperature sensors, and the like. The sensors may also include pressure sensors that detect back-resistance forces of the applied material for determining whether the material being applied has the correct proportion of material to water prior to use thereof. If the detected back-resistance forces are lower than a predetermined ideal back-resistance force, then the mixture of the material includes too much water. However, if the detected back-resistance forces are higher than the predetermined ideal back-resistance force, then the mixture of the material needs more water.

In embodiments of the invention the one or more sensors of the present electronic trowels may be a force meter that measures trowel application parameters comprising application time, trowel acceleration, trowel angle, and trowel directional movement, whereby these measured parameters are used to determine whether the material being applied is formulated correctly. The force meter may include one or more component parts that reside on and within the handle of the trowel. In these embodiments, an accelerometer may measure the trowel acceleration, a gyroscope may measure the trowel angle, and a magnetometer may measure the trowel directional movement.

Embodiments of the invention also relate to methods for applying a layer of material whereby a surface area is identified, a material for depositing on the surface area provided, and the material applied using a trowel having a handle, at least one blade, and one or more sensors residing on or within the trowel. The material is applied to the surface area using the trowel whereby, during the application process, the one or more sensors detect and collect installation data from the process of applying the layer of material over the surface area using the trowel. This installation data is transmitted to one or more electronic devices coupled to the one or more sensors, and is then analyzed using such electronic devices to identify and correct for any errors in the application of the material

BRIEF DESCRIPTION OF THE DRAWINGS

The features of the invention believed to be novel and the elements characteristic of the invention are set forth with particularity in the appended claims. The figures are for illustration purposes only and are not drawn to scale. The invention itself, however, both as to organization and method of operation, may best be understood by reference to the detailed description which follows taken in conjunction with the accompanying drawings in which:

DESCRIPTION OF THE PREFERRED EMBODIMENT(S)

Figure 1:
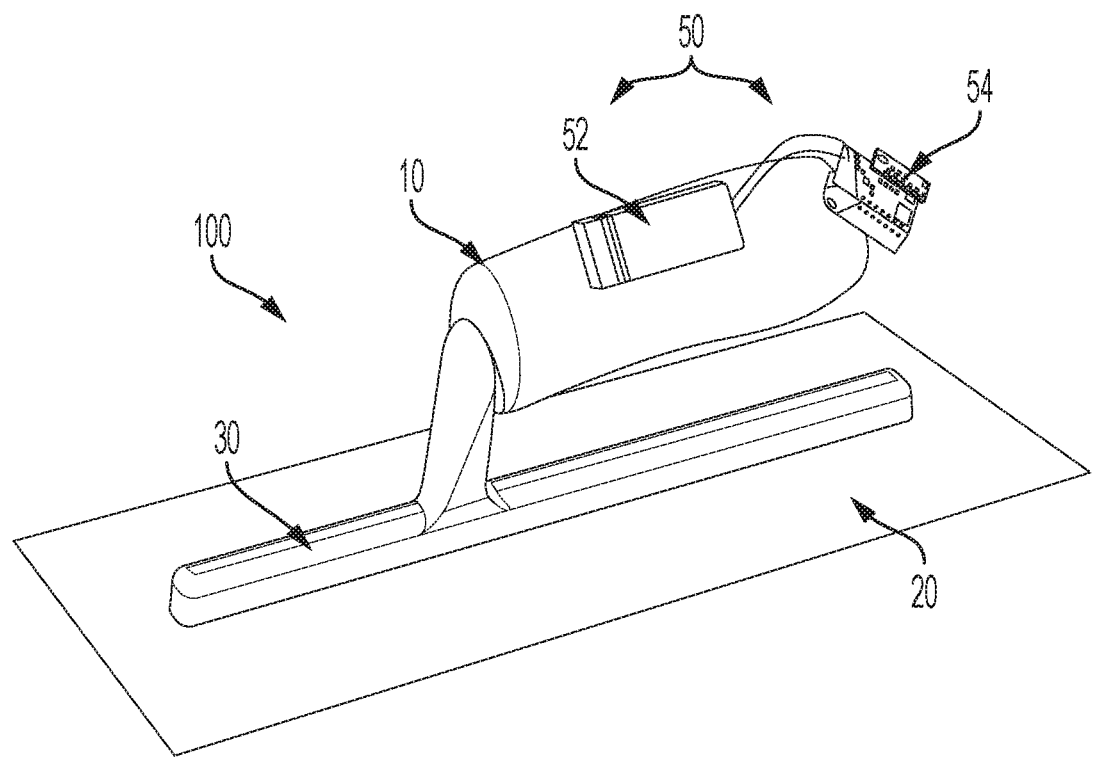
FIG. 1 illustrates a trowel having at least one electronic component for monitoring and controlling trowel usage and performance in accordance with embodiments of the invention.
Figure 2:
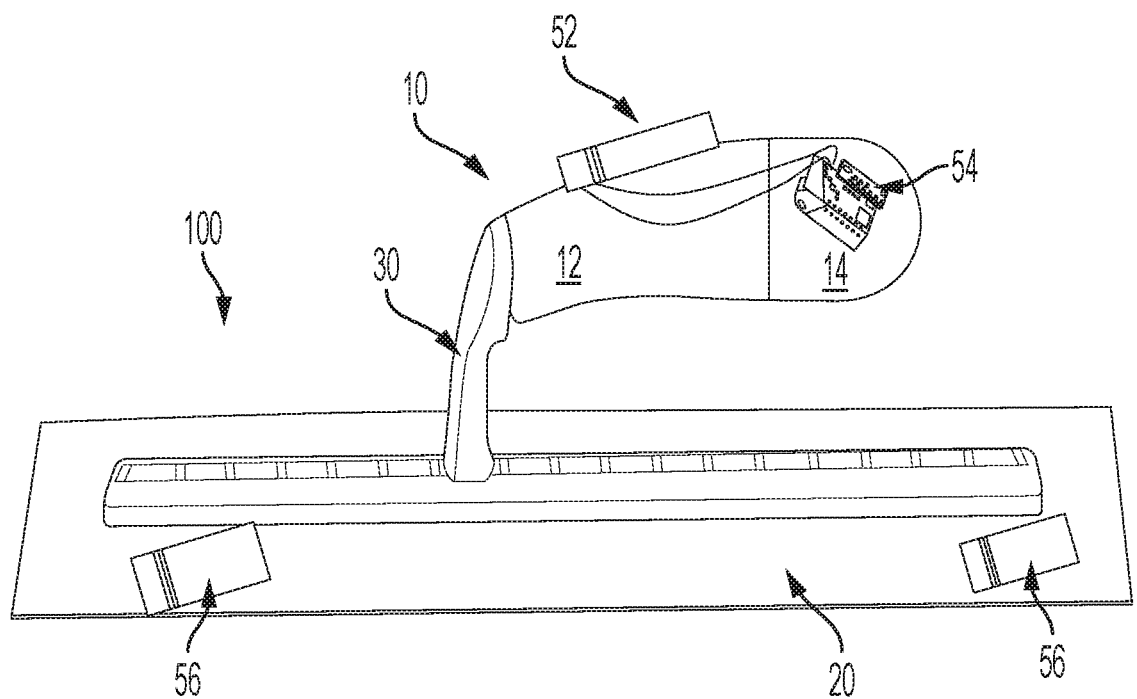
FIG. 2 illustrates a trowel having multiple electronic components for monitoring and controlling trowel usage and performance in accordance with various embodiments of the invention.
Figure 3:
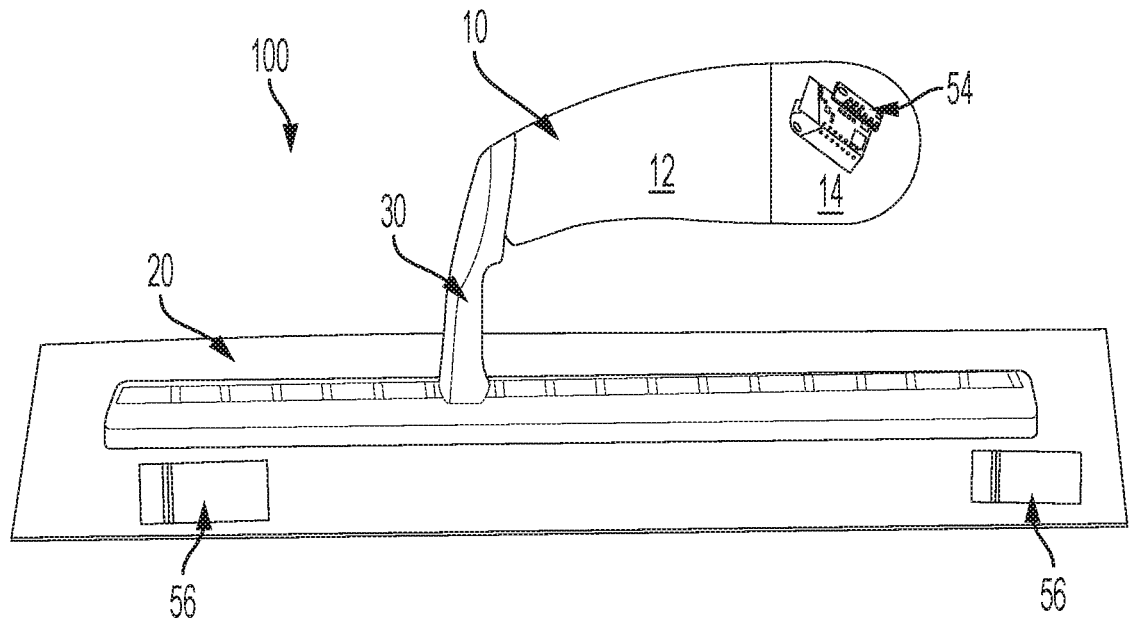
FIG. 3 illustrates other embodiments of one or more digital components on various locations of trowels in accordance with one or more embodiments of the invention.

In describing the preferred embodiment of the present invention, reference will be made herein to FIGS. 1-7 of the attached drawings, as well as the drawings detailed herein below.

Currently available trowels for use in masonry, concrete, construction, and applying adhesives (such as those used in tiling and laying synthetic flooring) include, but are not limited to, a bricklayer's trowel, pointing trowel, tuck pointing trowel, float trowel (finishing trowel), gauging trowel, pool trowel, margin trowel, notched trowel, and the like. However, each of these available trowels are limited in functionality since they only allow the installer to installing materials using such trowel, whereby the installer must assess, monitor, analyze and control the application process of such materials. That is, known trowels do not provide an installer any feedback during and/or after the material installation process. The challenge with improving the efficiency of tile installations is that there is not a ready supply of usage data from the end-user on the jobsite, short of doing an onsite observational study.

In accordance with the various embodiments, the invention provides a solution to conventional trowels that do not provide an installer with feedback during and/or after the material installation process. In one or more embodiments the invention provides systems, methods of making electronic trowels and the resultant electronic trowels 100 that provide an installer with feedback during and/or after the material installation process. While not meant to be limiting, the various trowels of the invention are capable of sensing and monitoring at least trowel usage, trowel performance, end-user performance, applied material properties as well as properties of the applied material itself. Various other attributes and parameters related to trowel usage, material applications, and trowel end-user work performance may be sensed, determined and analyzed in accordance with the various embodiments of the invention.

Trowels are often used in applying grouts, thin set mortars and other materials used in construction or flooring installation. Trowels are available as manual use hand-held trowels and mechanical powered trowels. In one or more embodiments, the invention is particularly suitable for use with manual use hand-held trowels, although it should be appreciated that the various components of the invention (i.e., sensors, monitors, electronics, digital components, smart components, etc.) are also suitable for use with standing and/or mechanical powered trowels.

The electronic trowels 100 of the invention are suitable for use in applying a variety of different materials including, but not limited to, masonry, concrete, construction, and applying adhesives, waterproofing or other tiling materials. Electronic trowels 100 of the invention are provided as electronic bricklayer trowels, electronic pointing trowel, electronic tuck-pointing trowel, electronic float trowel (electronic finishing trowel), electronic gauging trowel, electronic pool trowel, electronic margin trowel, electronic notched trowel, and various other electronic trowels.

For ease of understanding the invention, embodiments of the invention are described herein in relation to components of the invention affixed to or residing within or on manual use hand-held trowels. Again, it should be appreciated that the trowel of the invention may be a hand-held trowel, standing trowel or mechanical trowel. Referring to FIGS. 1-5F, various electronic trowels 100 of the invention are depicted. The hand-held trowels 100 may include at least one handle 10 attached to at least one base plate or blade 20 via at least one shank 30. The handle 10 may be composed of any type of material including, for instance, wood, plastic, metal, a composite material, and the like. As shown in the drawings, the handle 10 may be a short handle or a long handle, and the handle 10 may be attached to the blade 20 at single fixation end or two or more fixation ends. Suitable trowel handles 10 for use in the invention may have a variety of different shapes and sizes, whereby short handled trowels 100 are typically used for bending or kneeling troweling applications, while long handled trowels 100 are typically for standing trowel applications. The long handles allow installers to trowel materials (e.g., thin set mortar) without walking on such material, however, the pressures applied are often less than that applied with the short handle trowel.

The blade 20 of the present trowels 100 may have flat surface areas for applying and spreading the materials smoothly. The blades 20 typically have flat surface areas for applying and spreading the materials smoothly. Trowels 100 of the invention may have a single flat blade, multiple flat blades, or even v-shaped blades for forming angles. These blades 20 may be made of steel (e.g., blue steel, stainless, high-carbon steel, etc.), cast stainless steel, and the like. The trowel blades 20 may have a variety of different sizes and shapes. For instance, the blades 20 may have sizes ranging from about 8×3-inch, 14×4-inch trowel, a 16×4-inch trowel, or even trowel blades having lengths in feet (e.g., ranging from 2 to 4 feet). As shown in the drawings, suitable blade 20 shapes of the invention may vary. These blade shapes may include, but are not limited to, square, rectangular, oval, triangular, or even any of these shapes having rounded or square ends.

The various trowels 100 of the invention also include one or more electronic trowel sensory units 50 that may reside on the trowel, reside within parts of the trowel, may be permanently or removably attached/affixed to the trowel, or even comprise a part of the trowel. Various trowel sensory units of the invention, and suitable for use with the invention include, but are not limited, trowel sensory units that provide the abilities of at least sensing, recording, monitoring, and analyzing job site trowel usage data, trowel performance, material installation sufficiency, properties of materials being installed, properties of installation process, time of installation, and various other trowel usage, installation parameters, and end-user performance data. While the foregoing describes various uses and capabilities of the trowels 100 of the invention, it should be appreciated that the parameter being monitored may be any measure, feature or data associated or involved with the installation of materials using a trowel.

In one or more embodiments, the trowel sensory units 50 may be installed in, or on, any location of the trowel for obtaining desired installation data to enable proper material application to ensure reliable unflawed material installation. That is, referring at least to FIGS. 1 and 2, the trowel sensory unit 50 may be installed within or on the trowel handle 10. For instance, one or more sensors 50 may be installed on the handle 10 of the trowel either on a surface thereof or embedded/inserted into a cavity region of the handle 10, such that, the sensory unit 50 resides entirely within the handle 10. Alternatively, the sensory unit 50 may reside both within or on the handle 50 in combination with on the blade 20 portion of the trowel 100. Sensory units 50 may also be provided on the shank 30 portion of the instant trowels 100.

The trowel sensory units 50 of the invention may be digital and/or wireless sensors to provide current trowel usage data, end-user use and performance data, applied material property data, and the like (herein referred to as "trowel usage data"). Each trowel 100 may be provided with one or more sensory units 50 providing the ability to simultaneously measure various different installation and end-user parameters to ensure a reliable and quality end product. As shown in FIGS. 1-4 the trowel sensory units 50 include at least one sensor 52, 56 or 58, and at least one microprocessor 54 for monitoring, analyzing, storing and transmitting trowel usage data to one or more end-users. The use of multiple sensors in one or more locations of the trowel allows for various functionality parameters, data, and properties to be collected and analyzed simultaneously to ensure proper material installation using such trowel of the invention.

Figure 4:
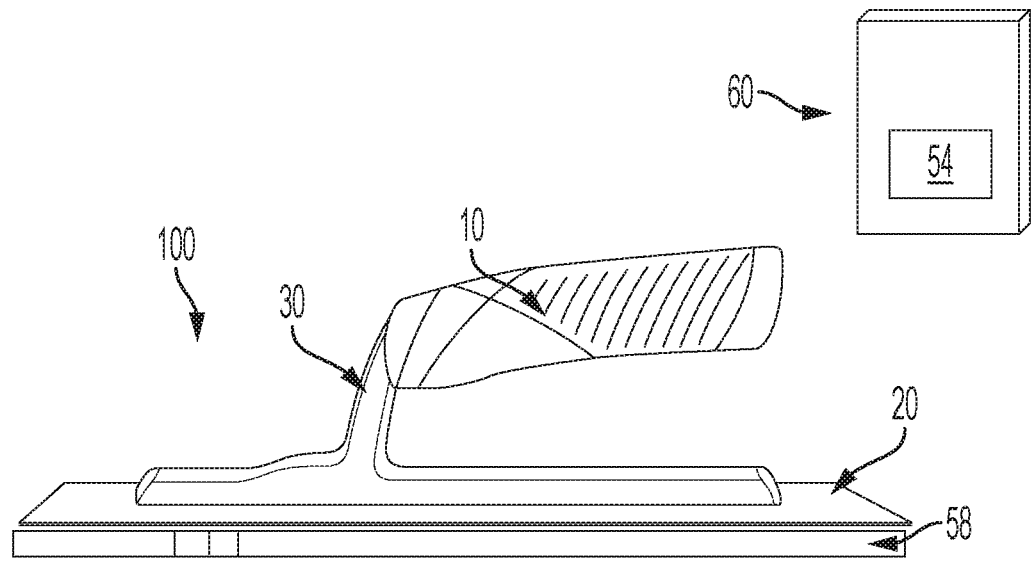
FIG. 4 illustrates still other embodiments of trowels of the invention having an electronic component attached to the bottom of the blade for monitoring and controlling trowel usage and performance in accordance with embodiments of the invention.
Figures 5A, 5B:
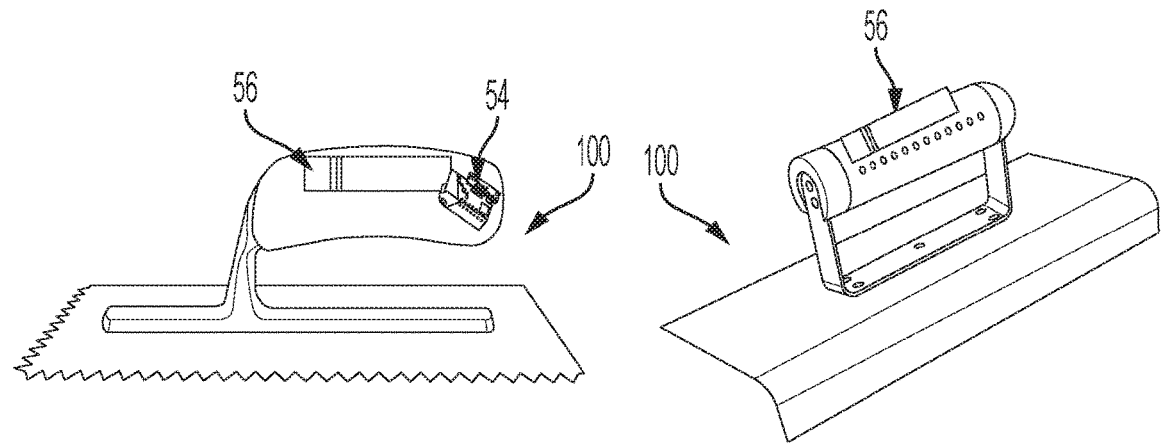
FIGS. 5A-5F illustrate various types of trowels suitable for use in the invention, each having one or more electronic components for monitoring and controlling trowel usage and performance in accordance with the invention.
Figures 5C, 5D:
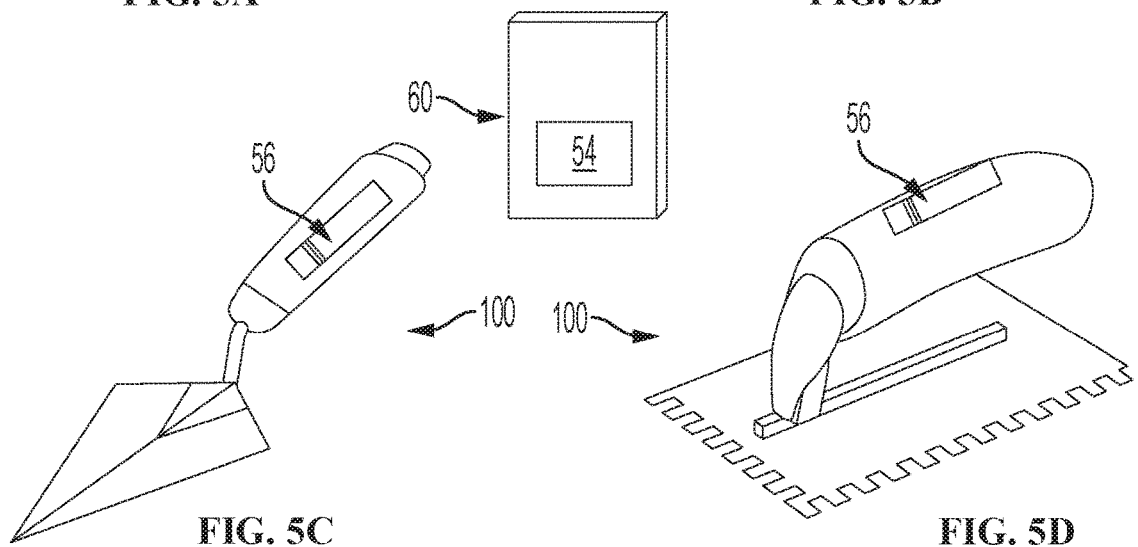
Figures 5E, 5F:
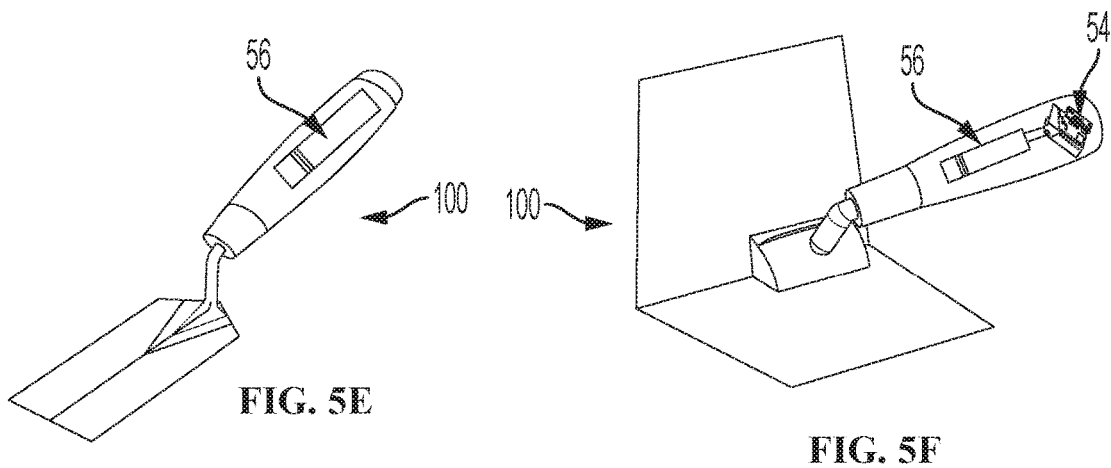

In one or more embodiments, the at least one sensor 52, 56 or 58 may comprise a sensor 52 that is physically connected to at least one microprocessor 54 (see, e.g., FIGS. 1 and 2), or a sensor 56 that is remotely connected to at least one microprocessor 54 (see, e.g., FIGS. 2, 3 and 4), or even a sensor 58 that is a part of the trowel itself (e.g., the sensor is the blade itself, or a component thereof) that is physically or remotely connected to at least one microprocessor 54 (see, e.g., FIG. 4).

Various sensors 52, 56, 58, etc. suitable for use in the invention may include one or more of the following sensors: temperature sensor/thermal/heat/temperature sensor (e.g., thermistors, thermocouples, IC, etc.), IR sensor, UV sensor, ultrasonic sensor, chemical sensor, electric current/electric potential/magnetic sensor, flow/fluid sensor, position/angle/displacement/distance/speed/acceleration sensors, proximity sensor, pressure sensor, level sensors, force sensor, density sensor, Hall-effect sensors.

The position/angle/displacement/distance/speed/acceleration sensors may include, but are not limited to, the following sensors: capacitive sensing, flex sensor, gyroscopic sensor, impact sensor, inclinometer, integrated circuit piezoelectric sensor, laser rangefinder, laser surface velocimeter, linear encoder, linear variable differential transformer (LVDT), photoelectric sensor, accelerometer, piezoelectric accelerometer, position sensor, position sensitive device, angular rate sensor, rotary encoder, rotary variable differential transformer, shock detector, shock data logger, ultrasonic thickness gauge, ultra-wideband radar, variable reluctance sensor, velocity receiver, moisture sensor, humidity sensor, speed sensor, mass, tilt sensor, force sensor, viscosity sensor, and the like, or combinations thereof.

All of the above sensors 52, 56, 58, etc. of the invention detect and collect data, which may then be transferred to and analyzed by an analytical device, such as, at least one microprocessor 54 (e.g., an integrated circuit (IC), computer, etc.). In one or more embodiments, the at least one microprocessor 54 of the sensory units 50 may include various integrated circuits (IC), computer software and analytics to analyze the on-site installation process, techniques and parameters. The analyzed trowel installation data may be stored (either on the trowel (e.g., a SIM card in/on the sensory unit attached to the trowel) or it may be stored remotely from the trowel (e.g., via Bluetooth device stored off the device on a computer/server).

The stored results may be reported to end-users after installation is complete for downstream analysis and creating a profile history of the trowel installed material and resultant product. For instance, on-site installation processing, techniques and parameter information collected with the instant digital trowel may include time spent tiling and not tiling, linear feet of tile laid, applied material coverage, applied material thickness, and the like.

In embodiments of the invention, the collected trowel usage data is configurable with a variety of design, layout, project, and software platforms. For instance, the collected trowel usage data may be configurable with AutoCAD, BIM, Sage, Procore, Microsoft Project, and the like. The collected trowel usage data may also be configurable and transmittable to a smart device 60 having at least one microprocessor 54. These transmissions may be made by WIFI, SIM card, USB port with internal drive, Bluetooth, cellular networks (e.g., 3G, 4G, 5G, etc.), as well as low frequency data exchanges with future smart devices. The various sensory units 50 of the invention may be powered by a battery cell, plug-in charge, plug-in charge with a battery, removable battery pack, wireless charging, etc.

The trowel sensory units 50 may further include one or more alert devices to notify an installer in real-time or during installation so that the installer can modify, adjust or correct installation features/parameters to ensure proper material application during the installation process. These alert devices may be a component within the sensors 52, 56, 58, etc. or the microprocessors 54 of the invention. Alert or notification devices suitable for use in the invention may include, but are not limited to, sound alert devices to send different signals based on either proper or improper material installation, display screen(s) having various visual notifications (e.g., different colors, numbers, text, graphical displays, etc.) to depict different features/parameters of the trowel and/or the material being installed during the installation process to ensure proper material application (e.g., to ensure sufficient material application thickness, area coverage, wetness, density, etc.), and the like.

While not meant to be limiting, the sensors 52, 56, 58, etc. of the invention may be one or more temperature sensors 56 residing, for instance, on the blade 20. These temperature sensors 56 may be infrared temperature readers for determining installation temperatures. Temperature is a key variable in the rate of applied material curing, and if temperatures are at risk for the material curing too fast, such data may be transmitted to the end-user that the applied material is at risk of flash setting. The end-user may then rectify the situation by adjusting hydration levels of the applied material (e.g., increasing amount of fluid mixed with applied material) since the amount of hydration affects cure rates. Alternatively, hydration levels of the applied material may be decreased depending upon the sensed temperatures which may jeopardize tile installation.

In certain embodiments the sensors 52, 56, 58, etc. may be one or more pressure sensors. The pressure sensors 58 may reside on the blade 20 to measure back resistance (force) of the applied material (i.e., the amount of resistance asserted on the trowel as the end-user moves back over the applied material. This back-resistance pressure measure may be used to determine quality of mixed applied material, that is, determine whether the applied material is mixed properly. For instance, if the applied material requires mixing with water prior to use thereof, the pressure sensors 58 provides a back-resistance measure that enables the end-user to determine if the material is mixed properly. The applied materials may be provided with an ideal back resistance measure (e.g. an ideal density), and if the measured back-resistance data from the sensors provides a lower measure than the ideal back resistance measure, then the end-user is able to ascertain that the applied material was mixed with too much water. The end-user may then adjust the material composition, or adjust the installation procedures to accommodate the improperly mixed material. Similarly, if the measure back resistance data is higher than the ideal measure, then it may be determined that the material was not mixed with enough water and adjustments made to correct the product.

In various embodiments of the invention pressure sensors 52 may also be provided on or within the handle 10. Like pressure sensors 58 on blade 20, these handle sensors 20 may also be used to detect, measure and provide force data during application of the applied materials. The measured forces may include back resistance forces, as well as forward movement forces to determine applied materials properties and end-user exertion force data. That is, the sensor may detect forces that the end-user experiences during use of the instant trowel 100, which may be used to monitor the health and safety of end-user employees, train on best practices, or identify other issues related to workman performance and product efficiency.

The sensors of the invention also include distance sensors that measure the linear feet or square feet the trowel moves, such that, the linear feet distance of tile to be installed may be determined (e.g., to determine the amount of tile needed). From this measured linear or square feet, in combination with the measured amount of time it took the installer to install the tile, worker performance may be ascertained to monitor workman job performance. Using this data, a company may maintain quality control over its workers to ensure job criteria and performance is met to company standards.

In addition to using the measured back resistance (force), the sensors of the invention may also determine the trowel angle during use, and based on the determined trowel angle in combination with the measured back resistance (force), the mix quality of the applied material may be determined. Other sensors suitable for use with the invention may include pH sensors, which may reside on the edges of the blade, bottom of the blade, or on the teeth of the blade to detect and measure the pH of the applied material to ensure mix quality.

Figures 6, 7:
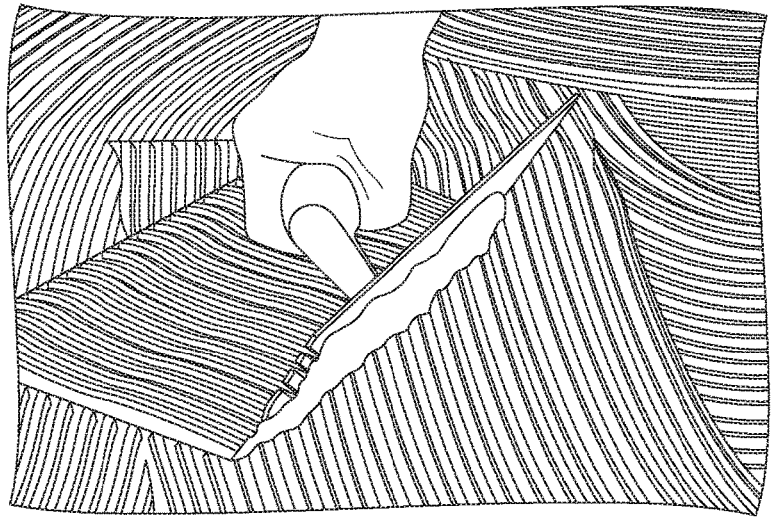
FIG. 6 illustrates an electronic trowel of the invention maintaining quality control of an applied material over a substrate in accordance with the invention.
FIG. 7 is a table depicting experimental results using an electronic trowel in accordance with various embodiments of the invention.

The sensors may also include movement sensors attached to any location of the trowel to detect any missed areas or slump of the edges of the applied material for ensuring quality and performance (e.g., when mortar is applied it must hold its lines and not collapse as shown in FIG. 6). The flex or flexibility of the blade 20 may also be measured using one or more flex movement sensors to ensure smooth and full coverage of the material being applied (spread) to the substrate. This may be desirable for trowels having flexible blue steel blades since too much flex may result in uneven or incomplete material application. These flex movement sensors on the present trowels 100 enable the installer to determine the degree of flexing of the blade, if any, and correct for any undesired or not enough flex of the blade to ensure proper material installation/application.

Other trowel working conditions may be obtained by providing the present trowels 100 with location sensors (e.g., GPS sensor) to determine and record usage locations, and durations thereof. In this manner, production schedules may be determined and set so that an entity (e.g., company/foreman) may manage its installers. These location sensors may also let the entity (e.g., company/foreman) know where work is being done for one or more days, and communicate such data back to project planning software that records and analyzes project progress as compared to the desired project schedule or timeline. Air quality sensors may also be secured on the trowel to provide feedback on VOC (volatile organic compounds) or other pathogens, containments, pollutants, etc. to ensure that the area is safe to work.

In one or more embodiments the sensors 52, 56, 58, etc. may be one or more optic sensors, or infrared or ultrasound sensors. The optic sensors may include optical light sensors positioned on any location of the trowel for scanning the material as it is being applied to ensure the material is being applied correctly. The optical light sensors may be programmed to detect applied material consistency, and any defects therein. The scanning may be a visual scan process that is recorded for downstream use, such as documentation that the material was applied correctly and/or the correct product was installed (e.g., to prove the correct color material was installed). The infrared or ultrasound sensors may be used alone or in combination with the optic sensors to scan the applied material and substrate. These measured data points may include, but are not limited to, data points from spatial dimensions, distance from the floor and height/width of the mortar placement, guaranteed coverage of the mortar over the substrate (goal is full coverage), material density readings to ensure homogenous mix quality, and the like. The optic sensors and/or infrared/ultrasound sensors may be positioned or reside on any location of the trowel. For instance, they may reside on or within the handle 10 to reach a wider array of data points, or a number of sensors may reside on edges of the blade, or even the blade itself may comprise the optic and/or infrared/ultrasound sensors.

In accordance with the various embodiments of the invention, the electronic trowels 100 of the invention provide users the ability of monitoring applied pressures, degree (angle) of pressure, amount of material in one or more selected areas (to make sure the mortar/thin set mortar is spread to completely cover the desired application area, and in sufficient amounts to provide a reliable product), patterns or techniques of applying materials (e.g., determine if material applied in straight lines or swirl pattern). The present trowels 100 provide capabilities of detecting, identifying, measuring, and analyzing trowel usage and end-user usage parameters.

The installer may be provided with such information so that the installer may correct any identified problems or deficiencies during trowel 100 usage to avoid problems of the prior art (e.g., avoid unsupported space or voids under the tiles (which may be created by trapped air, and may crack the applied tile or cause bond failure), avoid weak or uneven material spots that can be easily damaged by impact or heavy loads, minimize lippage, minimize tile breakage as well as other costly tile installation problems). The present electronic sensor trowels enable the installation of an accurately trowel installed area and tiled surface area, which is reliable, has strong bonds between the tile and the substrate, has adequate density and wear resistance, and is substantially unflawed, thereby avoiding tile cracking and/or debonding/delamination.

Referring to FIG. 7, experimental data from exemplary embodiments of the invention are depicted using an electronic trowel 100 of the invention having an embedded sensor unit 50. The sensor unit 50 was attached to the handle 10 of the trowel, and included a sensor 52 in combination with an analytical device comprising a microprocessor 54. The sensory unit 50 implemented was force meter comprising a SparkFun 9DoF Razor IMU M0, which includes a sensor combined with a microprocessor and provides a small, re-programmable, multi-purpose inertial measurement unit (IMU). The sensor and microprocessor were provided on and within the handle (e.g., incorporated into the hollowed-out handle of a trowel), respectively. The sensor unit 50 may be combined with a lithium battery and a microSD card to provide a digital electronic trowel in accordance with embodiments of the invention.

The sensory unit 50 implemented in FIG. 7 includes three-axis sensors, namely, an accelerometer, gyroscope, and magnetometer. Referring to FIG. 7, the parameters measured and recoded during trowel usage and material application included, but were not limited to, time, linear acceleration (accelerometer), angular rotation velocity (gyroscope), and magnetic field vector (magnetometer). The linear acceleration sensing captured force and speed data relating to the changes in movement of the trowel 100 in the x-axis, y-axis, and z-axis. The gyroscope sensing obtained the angle movements of the trowel during use in the x-axis, y-axis, and z-axis, and the magnetometer sensing measured the direction of the movement of the trowel in the x-axis, y-axis, and z-axis. The sensing unit with its sensors may be programmed to monitor, record data and log motion, transmit Euler angles over a serial port, or to even act as a step-counting pedometer.

Using the data of FIG. 7, an end-user or user is able to use the data to determine translation of degrees per second into coverage by using a conversion table of implied coverage at a specified angle to obtain optimal material coverage with superior performance and reliability in the finished product. For instance, using the data of FIG. 7 it may be determined that the trowel was moved 2 feet at an angle of 45 degrees in the north facing direction at a rate of 1 foot per second. When combining this information with time studies and analytics (e.g., using one or more of artificial intelligence (AI), machine learning techniques, and/or other analytical tools), it may be determined that 5 sq. ft. of tile was installed over 2 mins. Additional collected data detailed the number of passes prior to install, stoppage time, delays in installation, if the angle is in-line with installation guidelines, coverage, and the like.

The above sensor(s) and parameters measured are exemplary and are not meant to limit the invention in any manner. In the various embodiments of the invention, a variety of different types of sensors or detection devices may be included within or on a trowel. The trowel of the invention may be a hand-held trowel, standing trowel or mechanical trowel. It should also be appreciated that the sensors may be applied to other apparatus used to install or level a material over a substrate on which tiling is to be laid. For instance, sensors may be attached to or provided within a mechanical device used for automated tiling (not just in trowels—whether the trowel is a hand tool, standing tool or mechanical tool). In the various embodiments of the invention, the trowels 100 and all of the sensory units 50 may be waterproof to allow for easy cleaning thereof.

The electronic trowels 100 of the invention may be combined with software and/or trowel hardware for collecting ambient environmental conditions for installation. For instance, ambient conditions may be collected and combined with the trowel 100 via software using external resources (e.g., NOAA national oceanic and atmospheric association based on location), or using sensors on the trowel that collect humidity, dew point, temperature, and wind speeds, or even by manually entering such data into paired software. The electronic trowels 100 of the invention may also be used with video analytics and other job site sensors that all feed into project software to corroborate real-time productivity data during usage of the trowel 100.

While the present invention has been particularly described, in conjunction with a specific preferred embodiment, it is evident that many alternatives, modifications and variations will be apparent to those skilled in the art in light of the foregoing description. It is therefore contemplated that the appended claims will embrace any such alternatives, modifications and variations as falling within the true scope and spirit of the present invention.

Thus, having described the invention, what is claimed is:

1. An electronic trowel for applying a layer of material comprising:
    a trowel having a handle and at least one blade, the trowel is for applying a layer of material over a surface area;
    one or more sensors on the trowel detecting and collecting material installation data during application of the layer of material over the surface area using the trowel; wherein at least one of said one or more sensors comprise a sensor that detects working conditions of the application process for determining whether the mixture of the material being applied has a correct proportion of material to water; and
    one or more electronic devices coupled to the one or more sensors to receive and analyze the collected installation data for monitoring and controlling said application of the layer of material to ensure a desired end product is achieved.

2. The electronic trowel of claim 1 wherein the one or more electronic devices analyze the collected installation data to identify any errors in the application of the layer of material for correction by an installer during the installation process.

3. The electronic trowel of claim 1 wherein the one or more electronic devices analyze the collected installation data to identify any errors in the application of the layer of material for correction by an installer after the installation process.

4. The electronic trowel of claim 1 wherein the one or more sensors are attached to the handle of the trowel.

5. The electronic trowel of claim 1 wherein the one or more sensors are attached to the at least one blade of the trowel.

6. The electronic trowel of claim 1 wherein the trowel further includes a shank that attaches the handle to the blade, the one or more sensors are attached to the shank.

7. The electronic trowel of claim 1 wherein the one or more sensors comprise one or more blades of the trowel.

8. The electronic trowel of claim 1 wherein the one or more sensors are selected from the group consisting of temperature sensors, location sensors, infrared sensors, ultrasound sensors, pH sensors, movement sensors, and optical sensors.

9. The electronic trowel of claim 1 wherein the one or more sensors detect a height and a pattern of the applied layer of material for determining whether any slumping of ridges of the applied layer of material is present within the applied layer of material.

10. The electronic trowel of claim 9 wherein the one or more sensors comprise infrared sensors, ultrasound sensors, or movement sensors that detect the height and the pattern of the applied layer of material.

11. The electronic trowel of claim 1 wherein the trowel comprises a hand-held trowel, a standing trowel, or a mechanical trowel.

12. The electronic trowel of claim 1 wherein the one or more sensors are capable of capturing forces and stresses exerted on the end user for using in ensuring installer safety.

13. The electronic trowel of claim 1 wherein the one or more sensors detect a density of the layer of material to ensure a homogenous mixture of the material being applied.

14. The electronic trowel of claim 1 wherein the one or more sensors comprise temperature sensors that detect a temperature of the working conditions.

15. The electronic trowel of claim 1 wherein the one or more sensors comprise pressure sensors that detect back-resistance forces of the applied material for determining whether the material being applied has the correct proportion of material to water prior to use thereof, wherein detected back-resistance forces lower than a predetermined ideal back-resistance force indicate that the mixture of the material includes too much water, and wherein detected back-resistance forces higher than the predetermined ideal back-resistance force indicate that the mixture of the material needs more water.

16. The electronic trowel of claim 1 wherein the one or more sensors comprise at least one force meter that measures trowel application parameters comprising application time, trowel acceleration, trowel angle, and trowel directional movement, whereby these measured parameters are used to determine whether the material being applied is formulated correctly.

17. The electronic trowel of claim 16 wherein the at least one force meter comprises one or more component parts that reside on and within the handle of the trowel.

18. The electronic trowel of claim 16 wherein an accelerometer measures the trowel acceleration, a gyroscope measures the trowel angle, and a magnetometer measures the trowel directional movement.

* * * * *